(12) United States Patent
Robida (10) Patent No.: US 7,306,677 B2
(45) Date of Patent: Dec. 11, 2007

(54) CLAMPING FIXTURE FOR COATING STENTS, SYSTEM USING THE FIXTURE, AND METHOD OF USING THE FIXTURE

(75) Inventor: Todd Robida, Southbridge, MA (US)

(73) Assignee: Boston Scientific Corporation, Maple Grove, MN (US)

( * ) Notice: Subject to any disclaimer, the term of this patent is extended or adjusted under 35 U.S.C. 154(b) by 97 days.

(21) Appl. No.: 10/769,397

(22) Filed: Jan. 30, 2004

(65) Prior Publication Data

US 2005/0166841 A1   Aug. 4, 2005

(51) Int. Cl.
*B05C 13/00* (2006.01)
(52) U.S. Cl. .......................... 118/503; 118/66
(58) Field of Classification Search ........... 118/66, 118/64, 58, 70, 71, 300, 500, 503; 134/116, 134/115 R, 147, 153, 184; 269/48.1, 48.4; 279/2.1, 2.22, 2.17; 242/130.1, 571, 572; 68/205 R, 206, 205 E; 427/2.24, 2.25, 2.1, 427/2.28; 606/192, 198, 194, 108; 623/1.46, 623/1.47, 1.48, 1.1
See application file for complete search history.

(56) References Cited

U.S. PATENT DOCUMENTS

| | | | | |
|---|---|---|---|---|
| 1,805,801 A | * | 5/1931 | Boylan et al. | 118/400 |
| 3,434,675 A | * | 3/1969 | Zuckerman | 242/573.6 |
| 3,724,997 A | * | 4/1973 | Von der Eltz et al. | 8/484 |
| 3,796,185 A | * | 3/1974 | Boone | 118/325 |
| 3,989,001 A | * | 11/1976 | Brigham et al. | 118/679 |
| 4,893,623 A | * | 1/1990 | Rosenbluth | 606/192 |
| 5,091,205 A | | 2/1992 | Fan | |
| 5,788,979 A | * | 8/1998 | Alt et al. | 424/426 |
| 5,834,449 A | * | 11/1998 | Thompson et al. | 514/152 |
| 5,968,053 A | | 10/1999 | Revelas | |
| 6,306,163 B1 | * | 10/2001 | Fitz | 623/1.12 |
| 6,364,245 B1 | * | 4/2002 | Paal et al. | 242/560 |
| 6,572,644 B1 | | 6/2003 | Moein | |
| 2004/0013792 A1 | | 1/2004 | Epstein et al. | |
| 2004/0015224 A1 | | 1/2004 | Armstrong et al. | |

* cited by examiner

*Primary Examiner*—Brenda A. Lamb
(74) *Attorney, Agent, or Firm*—Kenyon & Kenyon LLP (57) ABSTRACT

A device is provided for holding an appliance from an interior that may include a center support shaft, two arbors arranged on the center support shaft in a spaced apart position, a plurality of springs coupled to the two arbors, and an actuator coupled to the center support shaft and adapted to decrease the distance between the two arbors. The device may be adapted to support a hollow cylindrical object from an inside of the hollow cylindrical object. The hollow cylindrical object may include a stent. When the actuator is actuated, the plurality of springs may be compressed and each spring may buckle in at least one buckle region. Actuating the actuator may cause the plurality of springs to expand and to clamp a stent. Deactuating the actuator may cause the plurality of springs to retract and to release a stent. A system for coating a medical appliance is provided. A method for coating a medical appliance is provided.

31 Claims, 8 Drawing Sheets

CLAMPING FIXTURE FOR COATING STENTS, SYSTEM USING THE FIXTURE, AND METHOD OF USING THE FIXTURE

FIELD OF THE INVENTION

The present invention relates to the manufacturing of medical appliances. More particularly, the present invention relates to a clamping fixture for spray coating stents that has automatic loading capabilities.

BACKGROUND INFORMATION

Medical devices may be coated so that the surfaces of the devices have desired properties or effects. For example, it may be useful to coat medical devices to provide for the localized delivery of therapeutic agents to target locations within the body, such as to treat localized disease (e.g., heart disease) or occluded body lumens. Localized drug delivery may avoid some of the problems of systemic drug administration, which may be accompanied by unwanted effects on parts of the body which are not to be treated. Additionally, treatment of the afflicted part of the body may require a high concentration of therapeutic agent that may not be achievable by systemic administration. Localized drug delivery may be achieved, for example, by coating balloon catheters, stents and the like with the therapeutic agent to be locally delivered. The coating on medical devices may provide for controlled release, which may include long-term or sustained release, of a bioactive material.

Aside from facilitating localized drug delivery, medical devices may be coated with materials to provide beneficial surface properties. For example, medical devices are often coated with radiopaque materials to allow for fluoroscopic visualization during placement in the body. It is also useful to coat certain devices to achieve enhanced biocompatibility and to improve surface properties such as lubriciousness.

Spray coating of stents may require a method of holding the stents that does not block the spray plume from uniformly coating the entire stent. Reducing contact with the stent and the desire to securely hold the stent may complicate the problem of clamping since the stent is subject to the forces from the spray plume itself. Excessive contact with the stent by the fixture during the spray coating operation may cause gaps in the coating that may result in loss of the coating during loading, shipping, and/or deployment of the stent. The coating may not adhere to the stent directly, and may only bind to itself, in which case the quality of the coating may depend on the coating being relatively uniform and relatively complete over the whole surface of the stent.

The flexible nature of the stent may require a clamping mechanism (also referred to herein as a fixing or affixing mechanism) that holds the stent from within to prevent the stent from sagging during the spraying operation. Coating self expanding stents greater than 40 mm may be difficult with current fixtures. Spray coating a stent that may be flimsy due to low stiffness and/or large size may be difficult due to the lack of rigidity of the stent itself. The lack of rigidity may make holding the stent complicated.

A fixture for mounting the stent(s) in the spray plume may meet the following criteria. The fixture may not block the spray plume from uniformly coating the entire stent. The number of contact points may be kept to a minimum to avoid causing bare spots in the coating. The fixture may hold the stent securely to prevent sagging of the center and/or ends when subjected to the forces from the spray plume (sagging of the stent may cause movement and may lead to poor coating). The loading and unloading of the fixture may be simple to keep handling damage to a minimum. The fixture may be easy to manufacture.

Some stent fixtures may be unable to hold a flimsy stent against the force of gravity and/or the spray plume. An extended version of a existing fixture has been used, but the conventional fixture may allow movement of the center of the stent, causing wavy and inconsistent coating through the middle and distal (loosest) end of the stent.

There thus is a need for a device for holding a stent during a coating operation that supports the stent against the forces of the coating operation and that does not inhibit the coating process.

SUMMARY

According to an exemplary embodiment of the present invention, a device for holding a stent during a coating and/or similar operation is provided. A clamp used to support a stent is provided. The clamp may include wires running along a center support shaft. The wire section profile may be round, flat, triangular, or any other appropriate shape. The wires may be expanded to clamp the stent and retracted to release the stent during loading and unloading operations. The opening and closing of the device may be controlled by a center actuating wire that may be either manually or automatically (electrically or pneumatically) actuated. The center actuating wire may be located inside the center support shaft.

The fixture may contact the stent only in enough places to provide the necessary support. A minimal contact area with the stent may reduce coating defects, thereby making a more robust and consistent coating. The fixture may be used in automated loading equipment in production to reduce stent fixing or affixing time. The automated loading equipment may minimize coating defects due to handling.

A device for holding an appliance from an interior may include a center support shaft, two arbors arranged on the center support shaft in a spaced apart position, a plurality of springs coupled to the two arbors, and an actuator coupled to the center support shaft and adapted to decrease the distance between the two arbors. A first end of each of the springs may be coupled to a first arbor and a second end of each of the springs may be coupled to a second arbor. The decrease of the distance may cause each of the plurality of springs to buckle. The buckling of each spring may increase at least one cross-sectional area defined by the device. The at least one cross-sectional area may be perpendicular to the center support shaft The device may be adapted to support a hollow cylindrical object from an inside of the hollow cylindrical object. The hollow cylindrical object may include a stent. The plurality of springs may include three springs. Each spring may include a wire section profile that is round, flat, or triangular. The actuator may be manually actuated, electrically actuated, or pneumatically actuated. The device may further include a center actuating wire situated inside the center support shaft and coupled to the actuator and the two arbors and adapted to decrease the distance between the two arbors. When the actuator is actuated, the plurality of springs may be compressed and each spring may buckle in at least one buckle region.

The first and/or the second arbor may be adapted to be controlled by the center actuating wire to cause the distance between the first and the second arbor to decrease or increase. Actuating the actuator may cause the first or the second arbor to move with respect to the other of the first and the second arbor. Actuating the actuator may cause the center support shaft to move with respect to the first or the second arbor. The device may further include a clasp assigned to a spring and arranged between the first and the second arbors. The clasp may couple the spring to the center support shaft. The clasp may define a plurality of buckle regions for the spring. The number of buckle regions may equal the number of clasps plus one. One clasp may be assigned to all springs and may be arranged centrally between the first and the second arbors.

The clasp may include at least two clasps arranged at different positions on the central support shaft. One buckle region defined by a clasp may be out of phase with another buckle region defined by another clasp.

Actuating the actuator may cause the plurality of springs to expand and to clamp a stent. Deactuating the actuator may cause the plurality of springs to retract and to release a stent. The device may further include a collects coupled to the center support shaft and adapted to be coupled to an end effector of a robot.

A system for coating a medical appliance may include an actuator coupled to a center support shaft, a collects coupled to the center support shaft, and an end effector of a robot coupled to the collects. The actuator may be adapted to decrease a distance between at least two arbors spaced apart on the center support shaft. The decrease of the distance may cause each of a plurality of springs to buckle. The buckling of each spring may increase a cross-sectional area perpendicular to the center support shaft.

The system may further include a center actuating wire situated inside the center support shaft and coupled to the actuator and the at least two arbors. The system may further include at least one of a sprayer and an atomizer for spraying a coating on to the medical appliance. The system may further include a drying rack adapted to accept the medical appliance after the coating operation and adapted to promote a drying of a coating applied to the medical appliance. The system may further include a lock adapted to secure the actuator in an actuated or an unactuated position. The system may further include an arrangement for cleaning the actuator, the center support shaft, the at least two arbors, the plurality of springs, the collects, and/or the end effector. The arrangement for cleaning may include a chemical bath, a chemical spray, and/or an ultrasonic cleaning apparatus. The system may further include an arrangement for weighing the medical appliance before and/or after the coating operation.

A method for coating a medical appliance may include inserting a center support shaft into an interior of the medical appliance, actuating an actuating wire coupled to two arbors arranged on the center support shaft in a spaced apart position, applying a coating to the medical appliance, and releasing the medical appliance.

A plurality of springs may be coupled to the two arbors. A first end of each of the springs may be coupled to a first arbor and a second end of each of the springs may be coupled to a second arbor. The method may further include buckling by each of the plurality of springs. The buckling of each spring may increase a cross-sectional area defined by the device. The cross-sectional area may be perpendicular to the center support shaft.

The actuating of the actuating wire may cause a distance between the two arbors to decrease. The method may further include blowing air or another gas at the medical appliance to dry the coating. The coating operation may include spraying a coating from a nozzle at the medical appliance. The method may further include moving the medical appliance or the nozzle so that the medical appliance and the nozzle are in close proximity. The method may further include moving the nozzle with respect to the medical appliance during the spraying. The releasing operation may include deactuating the actuating wire.

The method may further include cleaning the center support shaft, the actuating wire, two arbors, and/or the plurality of springs.

DETAILED DESCRIPTION

According to an exemplary embodiment of the present invention, a device and method for holding a medical device, especially a stent, from an inside surface is provided.

An exemplary embodiment of the present invention may include wire having a circular profile. In particular, stainless steel wire having a diameter of 0.009 inches may be used. Wire or springs having greater torsional rigidity may be possible and may prevent the wire from rolling over to one side of the center shaft, thereby holding the stent securely.

Figure 1:
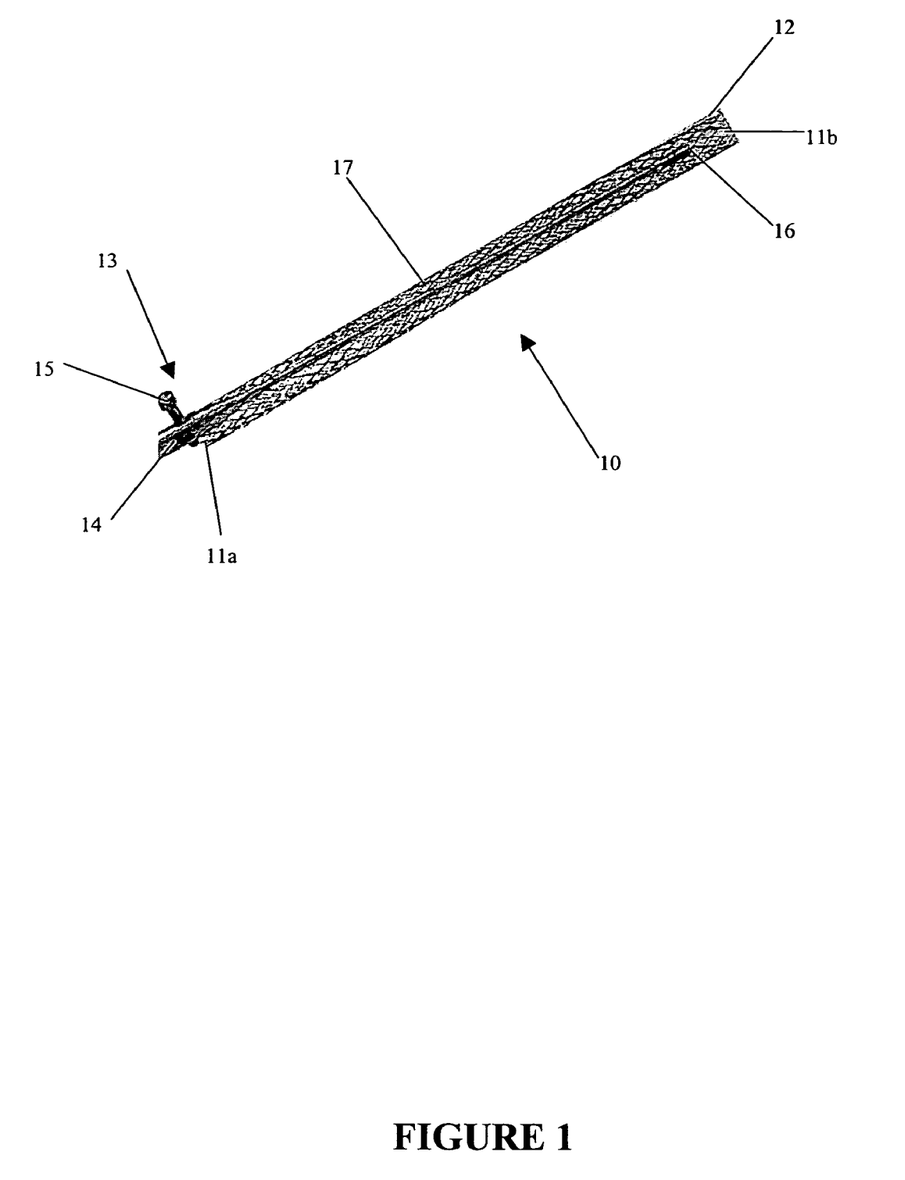
FIG. 1 illustrates an exemplary embodiment of the present invention in an expanded position holding a stent.

FIG. 1 illustrates an exemplary embodiment of fixture 13 in an expanded position holding stent 10. Sent 10 may be a hollow cylinder composed of struts 12 which interlink to form a fence-like structure and with two openings 11a, b. Central shaft 17 of fixture 13 may extend into opening 11a of stent 10 along a central axis of hollow stent 10. End 16 of fixture 13 extends toward, and may or may not extend out of, opening 11b of stent 10. Collects 14 of fixture 13 attaches to central shaft 17 and may be adjacent to opening 11a. Locking mechanism 15 of fixture 13 may extend out of collects 14 and may include a screw adapted to lock an actuating wire or rod into position.

Figure 2:
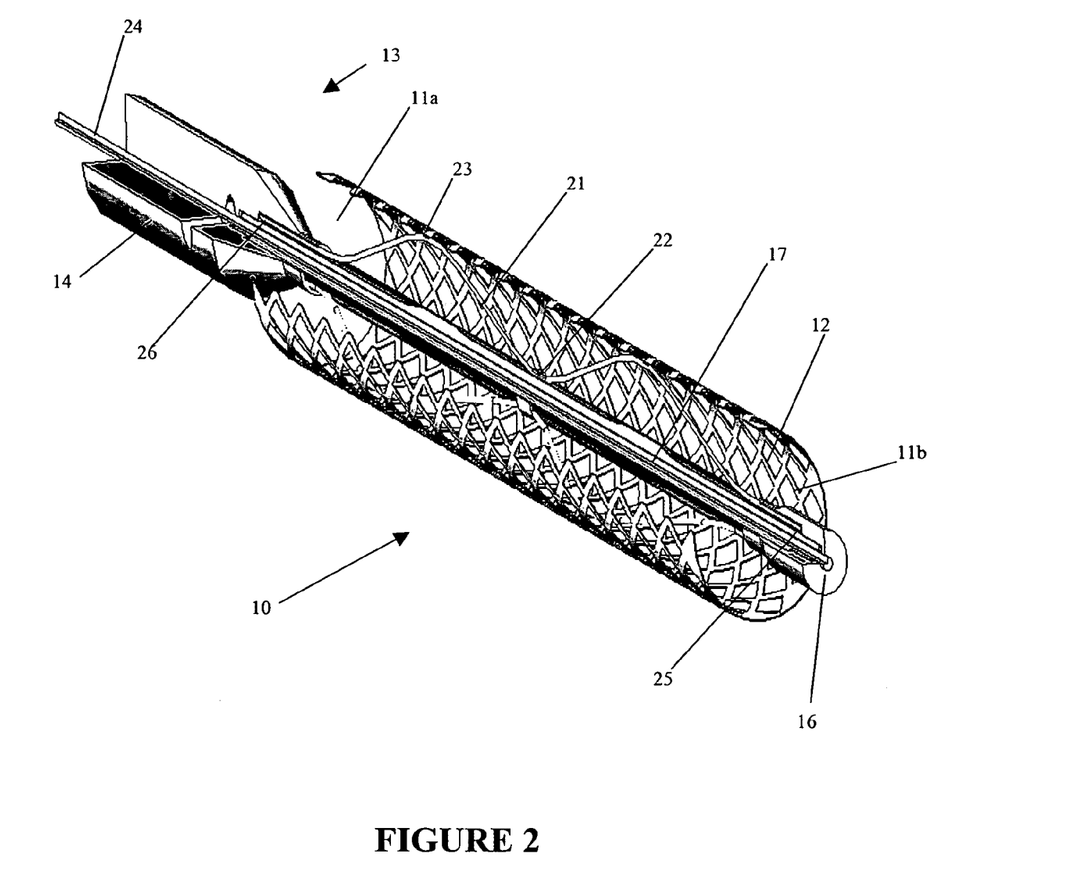
FIG. 2 illustrates a cross-sectional view of an exemplary embodiment of the present invention in an expanded position holding a stent with a portion cut-away.

FIG. 2 illustrates a cross-sectional view of an exemplary embodiment of fixture 13 in an expanded position holding stent 10 which has a portion cut-away. Sent 10 is composed of struts 12 and includes openings 11a, b. Fixture 13 includes center shaft 17 extending out of collects 14 and having end 16. As shown, end 16 of fixture 13 extends out opening 11b of stent 10. Wire 21 extends from collects arbor 26 in collects 14 to end arbor 25 at end 16. Collects arbor 26 and end arbor 25 anchor wire 21. Additionally, collects arbor 26 and end arbor 25 may anchor one or more additional wires. In one exemplary embodiment, collects arbor 26 and end arbor 25 may anchor a total of three wires arranged around central shaft 17 with an angle of 120 degrees between each adjacent wire. Wire 21 may or may not attach to central shaft 17 by clasp 22. Clasp 22 may or may not be movably attached to central shaft 17, and therefore may or may not slide along the length of central shaft 17 and/or wire 21.

In one exemplary embodiment, clasp 22 is slidably attached to central shaft 17 and fixedly attached to wire 21 at a position equidistant between collects arbor 26 and end arbor 25. In another exemplary embodiment, clasp 22 is fixedly attached to both central shaft 17 and wire 21 at a position equidistant between collects arbor 26 and end arbor 25.

Actuator 24 may be actuated by pulling, pushing, rotating, or by any other appropriate method. Actuating actuator 24 may cause fixture 13 to expand perpendicular to central shaft 17 by causing wire 21 to buckle. Wire 21 may be caused to buckle by moving end arbor 25 closer to collects arbor 26, by moving collects arbor 26 closer to end arbor 25, by moving both end arbor 25 and collects arbor 26 closer to each other, by moving both end arbor 25 and central shaft 17 closer to collects arbor 26, or by moving both collects arbor 26 and central shaft 17 closer to end arbor 25. Fixture 13 may expand by decreasing the distance between collects arbor 26 and end arbor 25, which may cause wire 21 (and any other wires anchored at collects arbor 26 and end arbor 25, or at any other arbors) to buckle. Each buckling of wire 21 (and any other wires) may create at least one buckle region 23. Additional buckle regions 23 for each wire 21 may be created by actuating actuator 24 if one or more clasps 22 attach wire 21 to central shaft 17.

Figure 3:
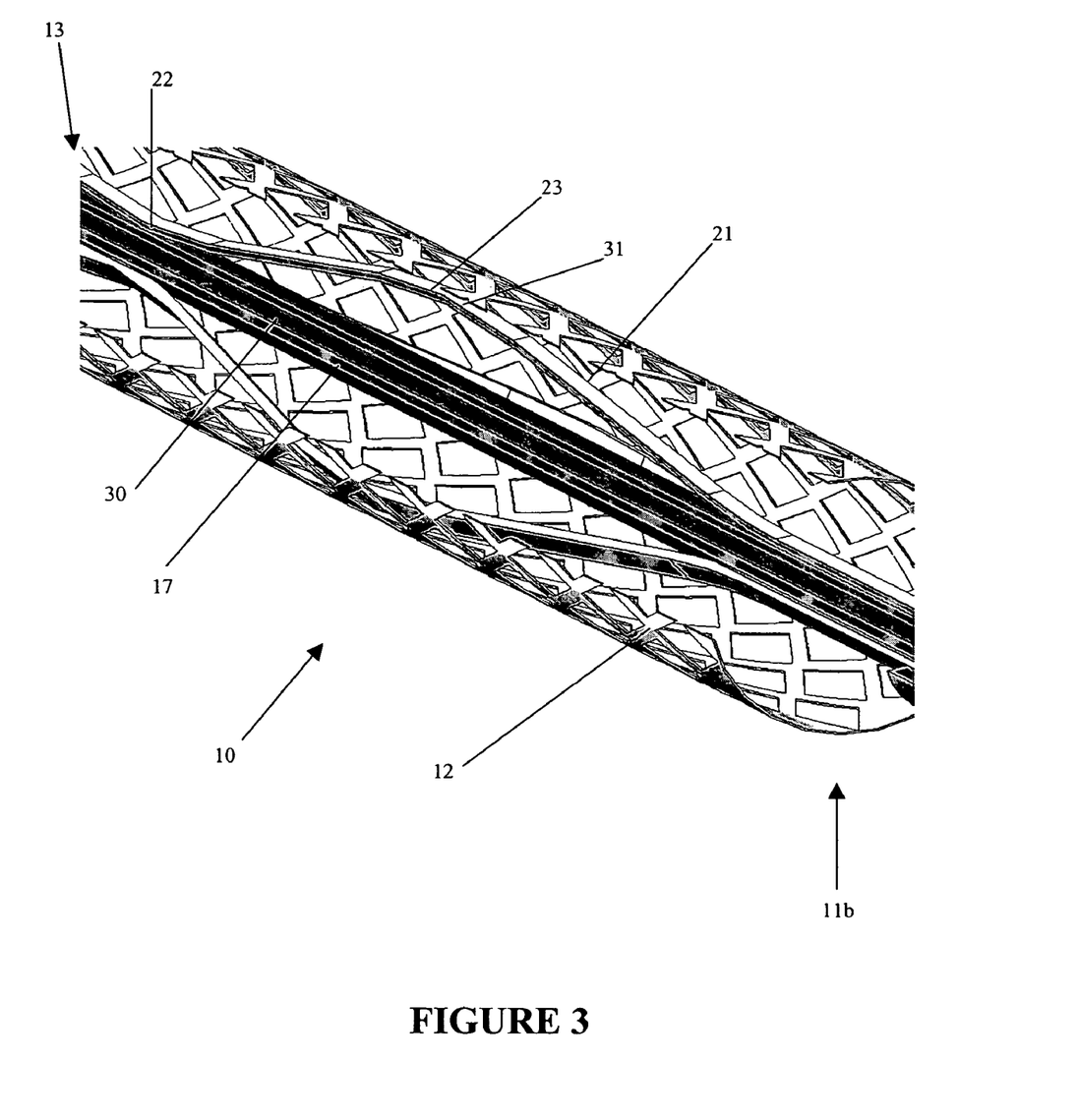
FIG. 3 illustrates a zoomed-in view of the exemplary embodiment of the present invention shown in FIG. 2.

FIG. 3 illustrates a zoomed-in view of a portion of the exemplary embodiment of fixture 13 shown in FIG. 2. Central shaft 17 extends along a central axis of stent 10 composed of struts 12. Central shaft 17 extends out opening 11*b* of stent 10. Fixture 13 is in an expanded position and includes clasp 22 holding wire 21 to central shaft 17. Actuating wire 30 extends down a central corridor of central shaft 17. Actuating wire 30 may cause an end arbor situated on the end of central shaft 17 to move proximally or distally with respect to a collects arbor and/or central shaft 17. Wire 21 may buckle when end arbor moves proximal to a collects, and may form one or more buckle regions 23. Buckle region 23 may form the area of the largest cross-sectional area of fixture 13, and may contact stent 10 at contact point 31. There may be three contact points (corresponding to three wires) spaced at 120 degrees on the interior of stent 10, and there may be one or more additional groups of three contact points if one or more clasps 22 are part of fixture 13. Contact point 31 may represent an area of stent 10 which may receive less coating material.

Figure 4:
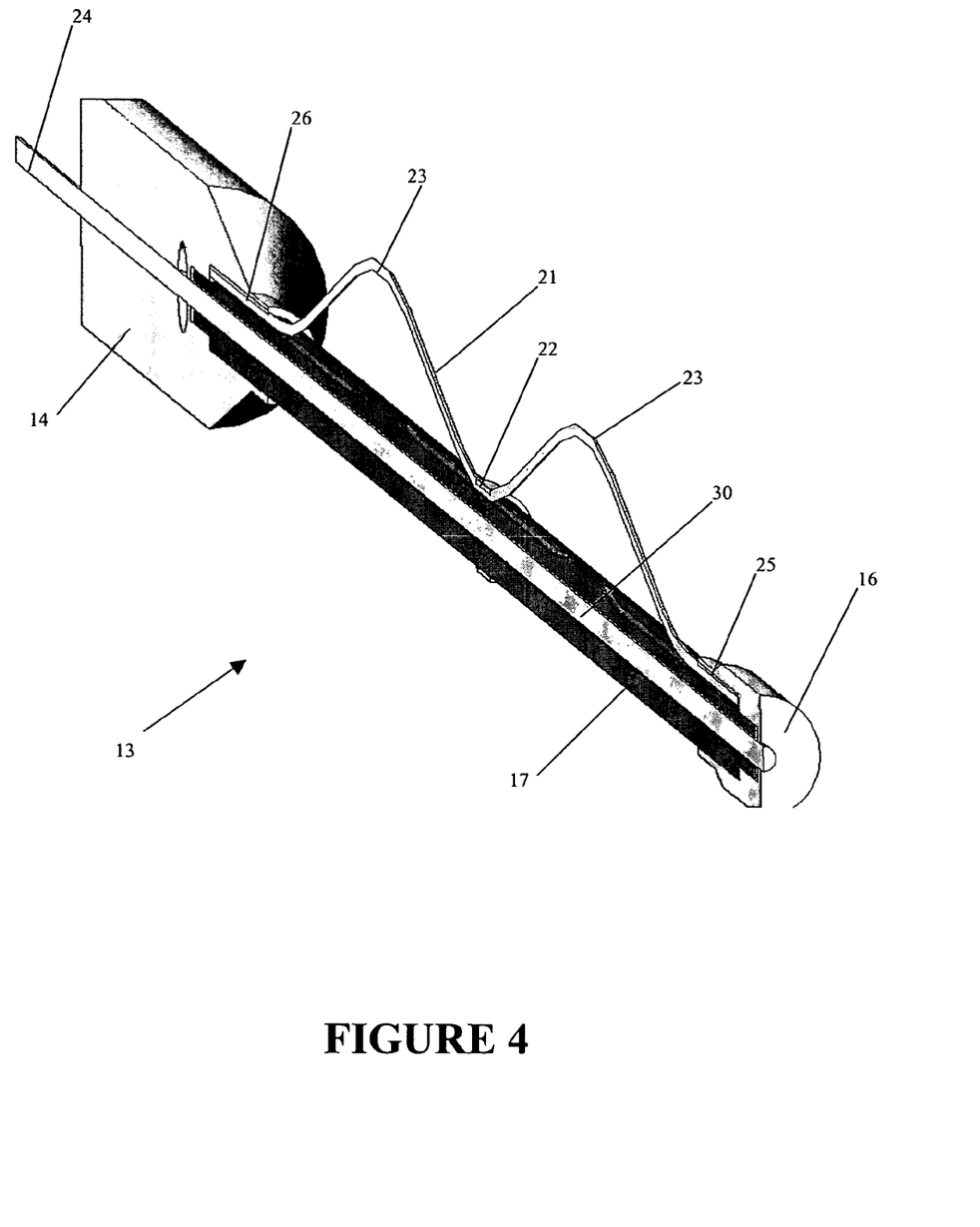
FIG. 4 illustrates a cross-sectional view of an exemplary embodiment of the present invention including two arbors and a center actuating wire.

FIG. 4 illustrates a cross-sectional view of an exemplary embodiment of fixture 13 in an expanded position without a stent and including collects arbor 26, end arbor 25, and center actuating wire 30. Only one wire 21 is shown in FIG. 4, though a plurality of wires may be used. Wire 21 anchors into collects arbor 26 on one end, in end arbor 25 on another end, and to clasp 22 attached to central shaft 17 in the middle. Center actuating wire 30 may be activated by actuator 24 to shorten the distance between collects arbor 26 and end arbor 25. This shortening may be accomplished by any of the several methods described above. Specifically, end arbor 25 may be drawn proximally by center actuating wire 30, and/or collects arbor 26 may be pushed distally by collects 14. Additionally, central shaft 17 may move proximally into collects 14 past arbor 26 and/or center shaft 17 may move distally towards end 16 of end arbor 25. The relative movement of collects arbor 26 and end arbor 25 may cause wire 21 to buckle in one or more buckle regions 23 which may define an area of largest cross-sectional area and therefore may define the diameter of the hollow medical appliance that may be held by fixture 13.

Another exemplary fixture design includes three leaf springs that expand to capture the inside of the stent. These springs can be expanded in at least two ways. For manual operation, the assembly may be compressed against a hard surface and locking screw(s) may be tightened. This may expand the leaf springs and lock them in place. For automatic operation, the center wire may be pulled to expand the leaf springs. The mounting feature on the fixture may match the production collets used in conventional stent coating operations.

An exemplary method for mounting and dismounting a stent from the fixture may include several steps. The mounting operation may include: ensuring that the leaf springs on the fixture are retracted prior to use; sliding the stent over the end of the fixture; and positioning the stent on a centering tool. These operations may locate the stent on the center of the fixture lengthwise. The next step in the mounting operation may be compressing the fixture against a hard surface until the leaf springs expand to retain the stent. The fixture may be provided with a hard stop when fully expanded. A socket head cap screw may be tightened sufficiently to retain the internal wire. The fixture may be removed from the centering tool. It may be possible to visually or otherwise check to determine that the stent is centered radially. The stent should not touch the center shaft of the fixture. If the stent is off center, pressure in the area where a leaf spring contacts the stent may relieve the problem.

Figure 5:
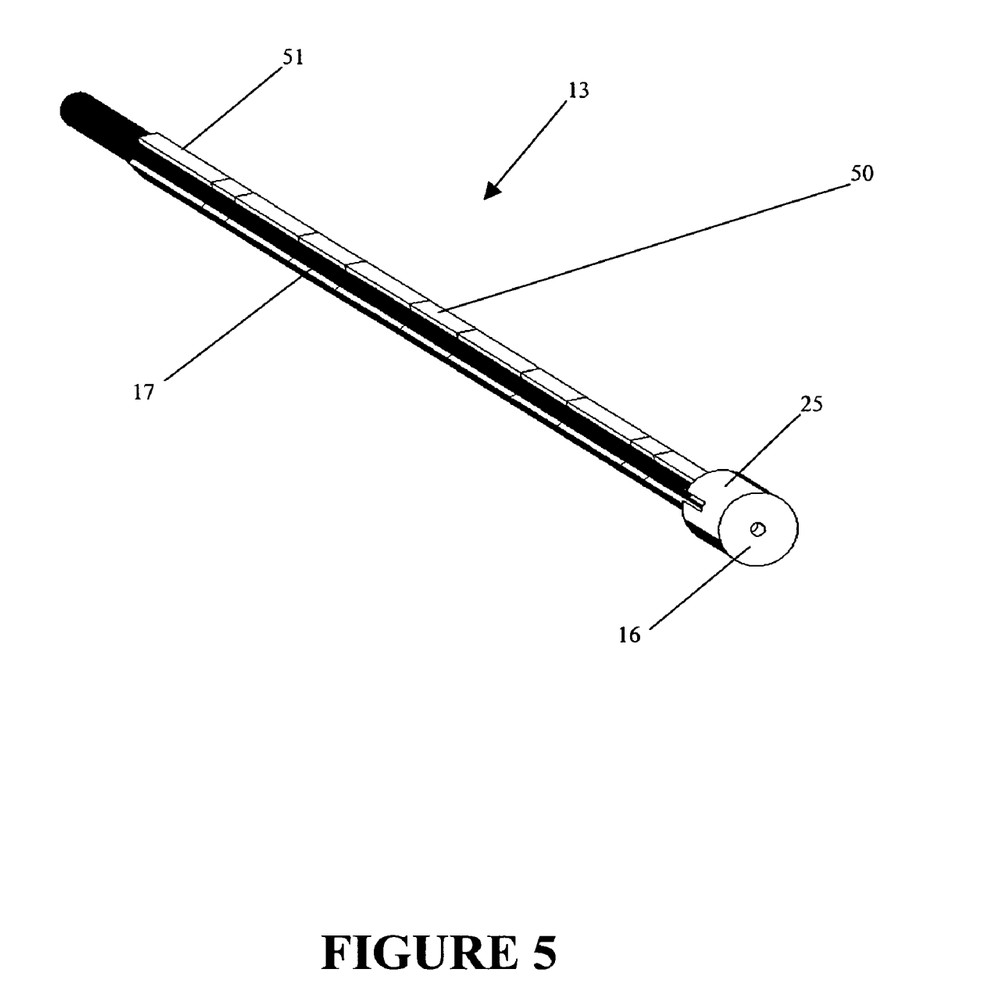
FIG. 5 illustrates a portion of an alternative exemplary embodiment of the present invention having leaf springs in an unactuated position.

FIG. 5 illustrates a portion of an alternative exemplary embodiment of fixture 13 having leaf spring 50 in an unactuated position. Leaf spring 50 is oriented parallel and adjacent to central shaft 17. There may be one or more additional leaf springs arranged around central shaft 17. In one exemplary embodiment, three leaf springs 50 are arranged equi-spaced around central shaft 17 with an angle of 120 degrees separating each leaf spring 50 from each adjacent leaf spring 50. One end of leaf spring 50 may anchor in end arbor 25, which also includes end 16. The other end of leaf spring 50 may anchor in anchor point 51.

Figure 6:
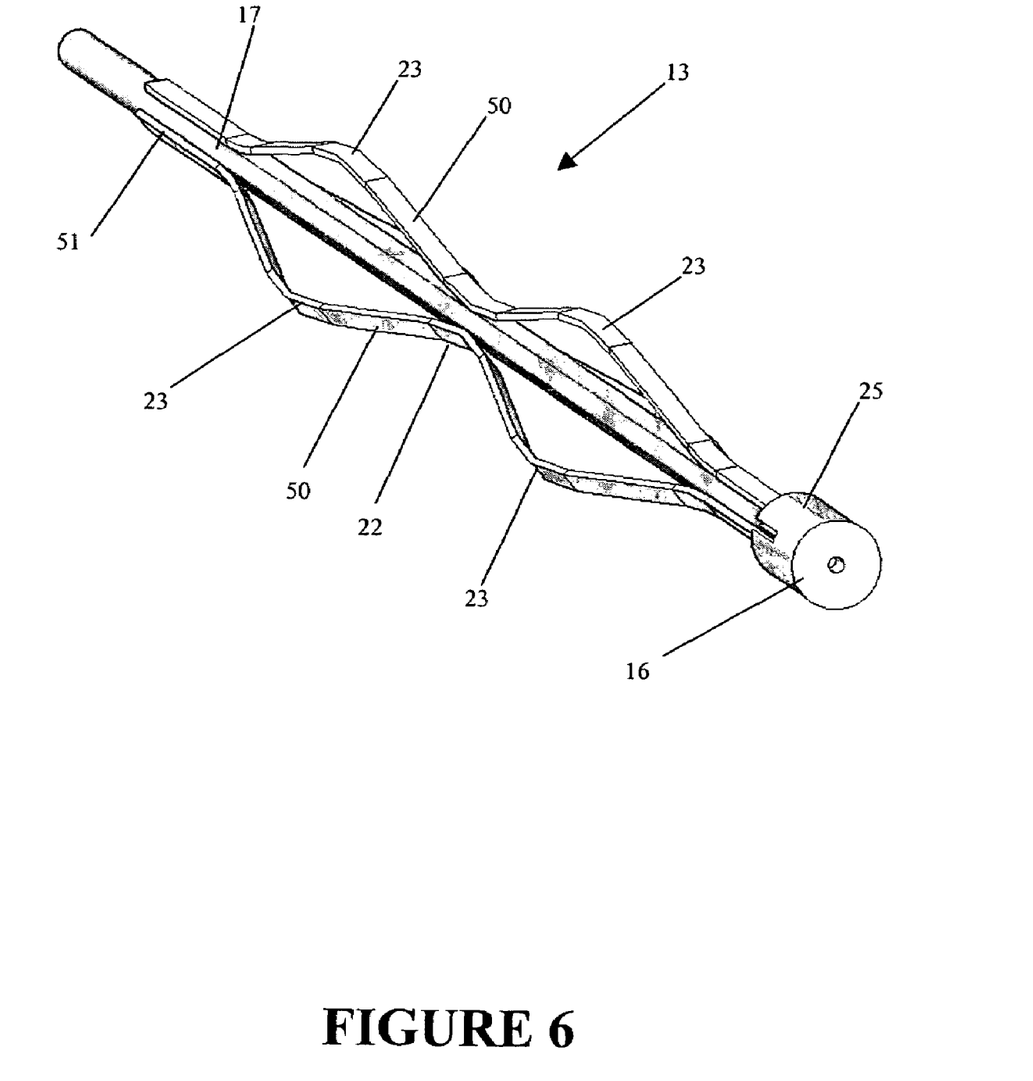
FIG. 6 illustrates a portion of the alternative exemplary embodiment of FIG. 5 shown in an expanded position.

FIG. 6 illustrates a portion of the alternative exemplary embodiment of fixture 13 shown in FIG. 5 shown in an expanded position. Two leaf springs 50 are anchored at anchor point 51 of central shaft 17 (which may be associated with an arbor), at the other end at end arbor 25, and/or in the middle at clasp 22. There may be one or additional leaf springs arranged around central shaft 17. In one exemplary embodiment, three leaf springs 50 are arranged equi-spaced around central shaft 17 with an angle of 120 degrees separating each leaf spring 50 from each adjacent leaf spring 50. End arbor 25 is arranged at end 16 of fixture 13. On each leaf spring 50, between anchor point 51 and clasp 22 and between end arbor 25 and clasp 22, is buckle region 23. Four buckle regions 23 are shown in FIG. 6, though more or fewer buckle regions may be possible. In an exemplary embodiment, the number of buckle regions for each leaf spring 50 (or alternatively, wire) may equal the number of clasps associated with that leaf spring 50 (or wire) plus 1. For example, each leaf spring 50 shown in FIG. 6 has one clasp (as shown in FIG. 6, the same clasp), and therefore the number of buckle regions equals two for each leaf spring (one plus one). Therefore a set of three leaf springs having the configuration shown in FIG. 6 may have a total of six buckle regions. Additionally, for this configuration the buckle regions define three points equi-spaced around a circle separated from a parallel circle having another three points equi-spaced around it. A line running through the center of each circle (corresponding to central shaft 17) may be perpendicular to each of the two circles. Alternative configurations for clasps, including clasps for fewer than all leaf springs 50 (or wires), and including clasps causing the sinusoidal or other curving shape of leaf springs 50 (or wires) to be out of phase with each other, are also possible.

Figure 7:
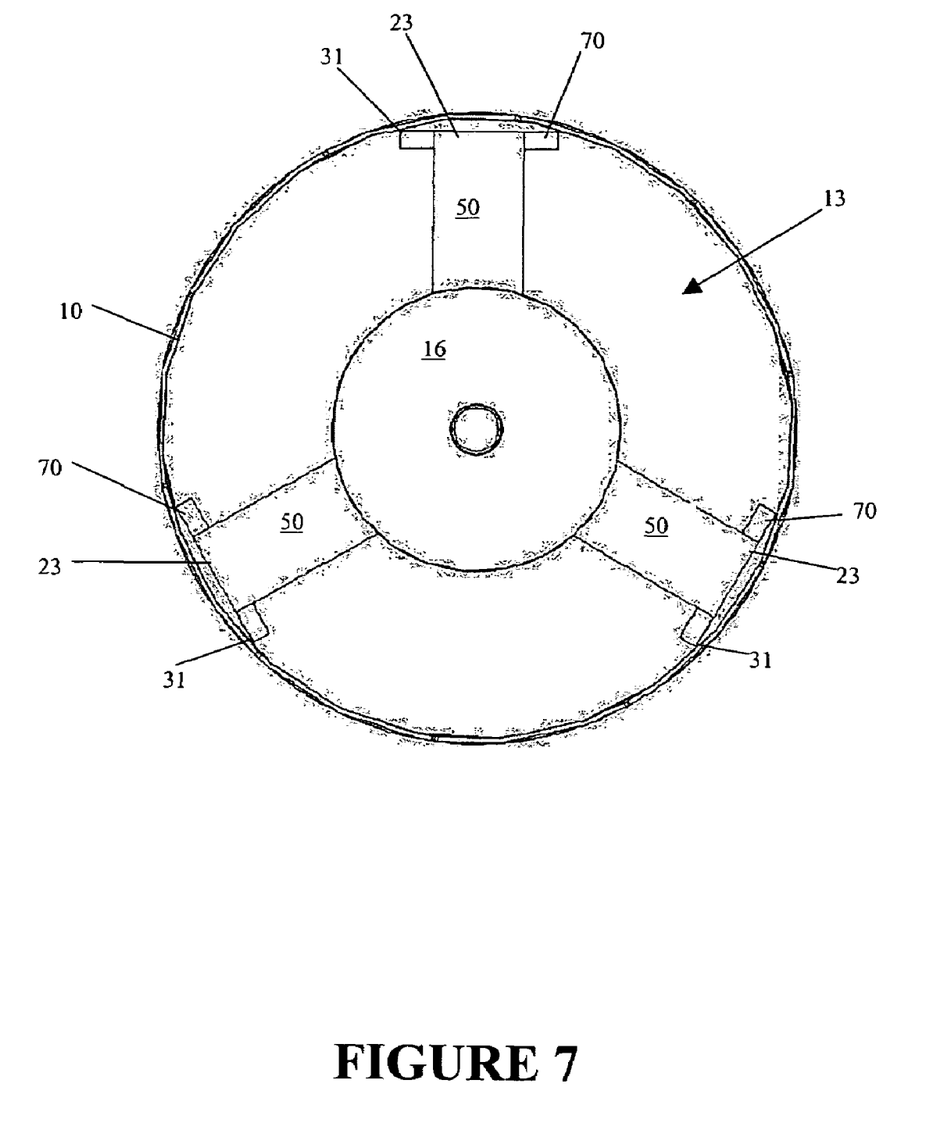
FIG. 7 illustrates the alternative exemplary embodiment of FIGS. 5 and 6 shown in an expanded position from an end-on perspective.

FIG. 7 illustrates the alternative exemplary embodiment of fixture 13 of FIGS. 5 and 6 shown in an expanded position from an end-on perspective towards end 16. Fixture 13 is shown holding stent 10. Three leaf springs 50 are spaced around fixture 13 and are separated by angles which may be equal and may be about 120 degrees. Buckle regions 23 may be the apex of the bending in leaf springs 50. Contact points 31 identify where fixture 13 contacts stent 10. Contact points 31 correspond to barbs 70, which are areas of greater lateral (perpendicular to the center support shaft) extension and which may be integral or attached.

Barbs 70 may be localized in buckle regions 23 or may be spaced along the length of leaf springs 50 (or wires). Barbs 70 may increase the lateral stability of stent 10 as it is held by fixture 13 by increasing the pressure at contact points 31. Additionally, barbs 70 may decrease the total area that fixture 13 covers during the coating of stent 10 (the total area of contact points 31), and therefore may increase the quality and contiguity of the coating of stent 10. Alternatively, springs having a triangular cross-section maybe utilized.

An exemplary method for dismounting the stent from the fixture may include loosening locking mechanism 15, which may be a socket head cap screw. The leaf springs may retract to release the stent. If the leaf springs do not retract enough to release the stent automatically, the end of the wire may be pushed and/or the free arbor may be pulled. Pushing and/or pulling may release the leaf springs.

An exemplary method for removing the stent may avoid pulling the stent off over expanded leaf springs in order to avoid damaging the polymer coating. The fixture may be soaked in solvent between uses to ensure that the mechanism does not get gummed up with polymer. Cleaning may be required less often than after each use.

Figure 8:
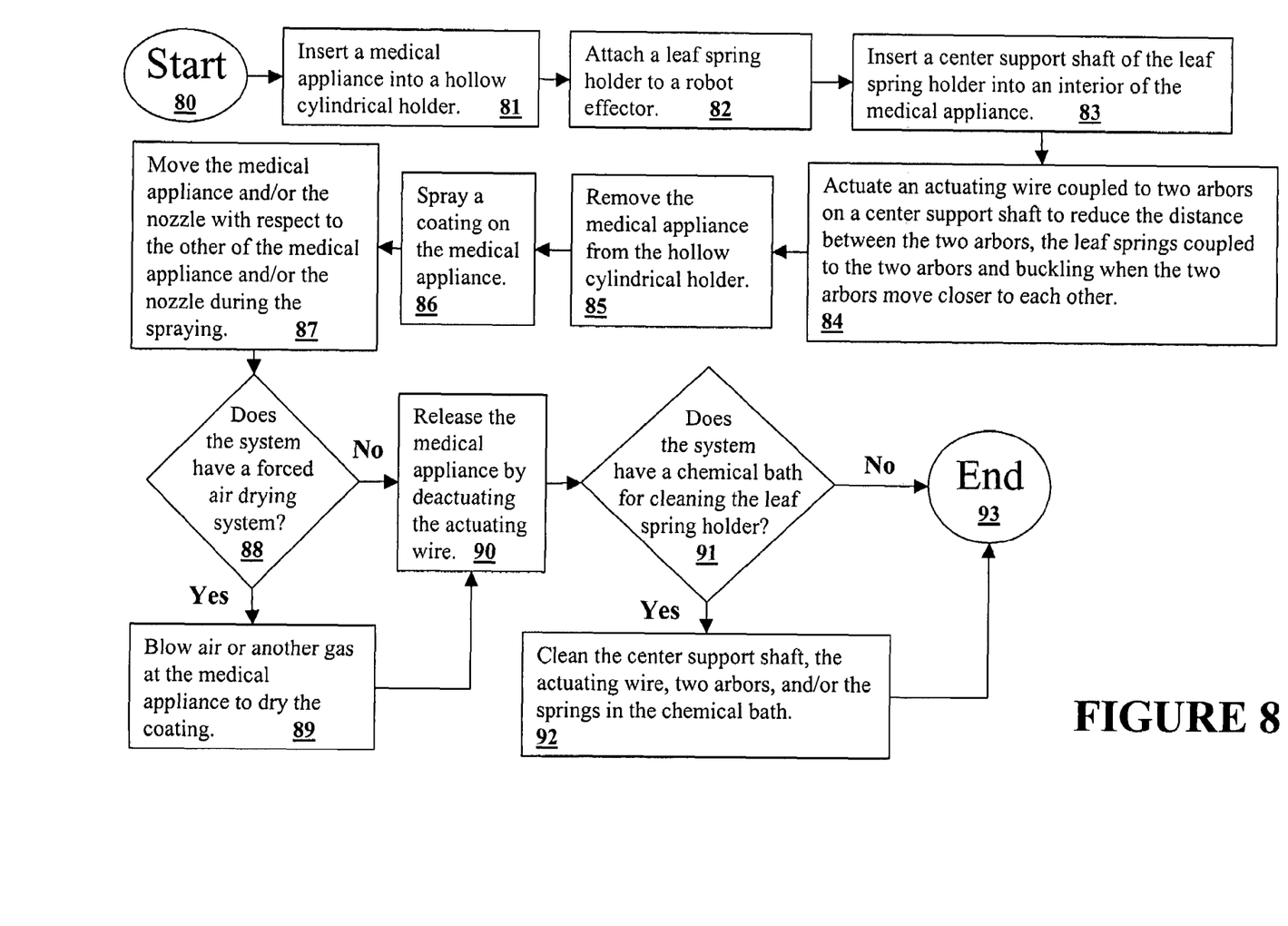
FIG. 8 is a flow chart illustrating an exemplary method according to the present invention.

FIG. 8 is a flow chart illustrating an exemplary method according to the present invention. The flow starts in start circle 80 and proceeds to action 81, which indicates to insert a medical appliance into a hollow cylindrical holder. From action 81, the flow proceeds to action 82, which indicates to attach a leaf spring holder to a robot effector. From action 82, the flow proceeds to action 83, which indicates to insert a center support shaft of the leaf spring holder into an interior of the medical appliance. From action 83, the flow proceeds to action 84, which indicates to actuate an actuating wire coupled to two arbors on a center support shaft to reduce the distance between the two arbors. The leaf springs are coupled to the two arbors and buckle when the two arbors move closer to each other. From action 84, the flow proceeds to action 85, which indicates to remove the medical appliance from the hollow cylindrical holder. From action 85, the flow proceeds to action 86, which indicates to spray a coating on the medical appliance. From action 86, the flow proceeds to action 87, which indicates to move the medical appliance and/or the nozzle with respect to the other of the medical appliance and/or the nozzle during the spraying.

From action 87, the flow proceeds to question 88, which asks whether the system has a forced air drying system. If the response to question 88 is affirmative, the flow proceeds to action 89, which indicates to blow air or another gas at the medical appliance to dry the coating. From action 89, the flow proceeds to action 90, which indicates to release the medical appliance by deactuating the actuating wire. From action 90, the flow proceeds to question 91, which asks whether the system has a chemical bath for cleaning the leaf spring holder. If the response to question 91 is affirmative, the flow proceeds to action 92, which indicates to clean the center support shaft, the actuating wire, two arbors, and/or the springs in the chemical bath. From action 92, the flow proceeds to end circle 93. If the response to question 88 is negative, the flow proceeds to action 90. If the answer to question 91 is negative, the flow proceeds to end circle 93.

An exemplary manufacturing use may include mounting the fixture on an automated arm that may allow a stent to be loaded into a production machine in a vial. The machine may handle the pre-coating weighing, coating, drying, and post-coating weighing operations on the stent. This may minimize coating damage from handling. The fixture may be actuated with a pneumatic or electric actuator using the internal wire. A production machine may also include a fixture cleaning station. Multiple fixtures in the machine may allow for more efficient loading, coating, unloading, and cleaning. Cleaning may need to be done after each, or after several, stent coating operations. Use of an exemplary fixture according to the present invention in production may reduce damage to a stent from operator handling as well as reduce the number of hand operations, thereby increasing efficiency.

Alternative exemplary embodiments may include various other features. The ability to clean and reuse the fixture may be possible, and cleaning the fixture may prevent the mechanism from sticking due to polymer buildup. Teflon or stainless steel bands may be used as clasps or bands to prevent movement of the center of the leaf springs away from the center shaft. Teflon shrink tubing may hold the middle of the leaf springs adjacent to the center shaft. A band that is easily removed and replaced may be beneficial. The band may attach to the center shaft. Tooling to assemble the fixture may be helpful. Smooth movement of the mechanism may be possible by deburring, a tolerance study, and/or appropriate leaf spring thickness selection, among other things.

An exemplary embodiment of the present invention may be adapted to stents as long as 120 mm or more by scaling up the design to handle these lengths. The fixture may contain extra features that allow flexibility for testing the design. For instance, the fixture may allow different thickness leaf springs to be attached. Leaf springs may be selected to provide an appropriate resistance, and an exemplary embodiment may use leaf springs with a thickness of 0.008 inches.

The leaf springs may be rectangular with barbs to retain the stents. Small barbs may tie the leaf springs into the teflon band. To further minimize contact area with the stent, the leaf spring may be made in an hourglass shape in which the necked-down regions contact the stent. In this situation, the rectangular cross-section of the leaf spring may be maintained in the regions near the attachment points to the center support shaft (e.g., the arbors and the buckle(s)), while the area near the buckle regions may be etched or machined so that the cross-section of the spring is a square or approximates a square. In this manner, the contact point with the stent may be minimized, while the strength of the leaf spring (compressively and torsionally) may be maintained.

The expansion of the leaf springs and the shape and material of the leaf spring may be adjusted to apply an appropriate amount of pressure to the inside of the stent. The profile of the leaf springs may also be modified to further minimize contact with the stent by utilizing triangular wire stock. One of the flat sides may contact the center shaft and the opposite corner may contact the stent. The triangular wire may have a cross-sectional area forming an isosceles triangle. This triangular wire may have a height from the base side of 0.040 inches.

During the loading and/or unloading of the stent from the fixture, the wire may be retracted. During the spray coating of the stent, the wire may be expanded to hold the stent from the inside. To actuate the mechanism, the arbors may be drawn together by pulling on the center actuating shaft. The center actuating shaft may be free to slide inside the center support shaft. Drawing the arbors together may cause the wires to buckle and extend from the center support shaft.

Medical implants are used for innumerable medical purposes, including the reinforcement of recently re-enlarged lumens, the replacement of ruptured vessels, and the treatment of disease such as vascular disease by local pharmacotherapy, i.e., delivering therapeutic drug doses to target tissues while minimizing systemic side effects. Such localized delivery of therapeutic agents has been proposed or achieved using medical implants which both support a lumen within a patient's body and place appropriate coatings containing absorbable therapeutic agents at the implant location. Examples of such medical devices include catheters, guide wires, balloons, filters (e.g., vena cava filters), stents, stent grafts, vascular grafts, intraluminal paving systems, implants and other devices used in connection with drug-loaded polymer coatings. Such medical devices are implanted or otherwise utilized in body lumina and organs such as the coronary vasculature, esophagus, trachea, colon, biliary tract, urinary tract, prostate, brain, and the like.

The term "therapeutic agent" as used herein includes one or more "therapeutic agents" or "drugs". The therapeutic agent may be any pharmaceutically acceptable agent such as a non-genetic therapeutic agent, a biomolecule, a small molecule, or cells.

Exemplary non-genetic therapeutic agents include anti-thrombogenic agents such heparin, heparin derivatives, prostaglandin (including micellar prostaglandin El), urokinase, and PPack (dextrophenylalanine proline arginine chloromethylketone); anti-proliferative agents such as enoxaprin, angiopeptin, sirolimus (rapamycin), tacrolimus, everolimus, monoclonal antibodies capable of blocking smooth muscle cell proliferation, hirudin, and acetylsalicylic acid; anti-inflammatory agents such as dexamethasone, rosiglitazone, prednisolone, corticosterone, budesonide, estrogen, estrodiol, sulfasalazine, acetylsalicylic acid, mycophenolic acid, and mesalamine; anti-neoplastic/anti-proliferative/anti-mitotic agents such as paclitaxel, cladribine, 5-fluorouracil, methotrexate, doxorubicin, daunorubicin, cyclosponne, cisplatin, vinbiastine, vincristine, epothilones, endostatin, trapidil, and angiostatin; anti-cancer agents such as antisense inhibitors of c-myc oncogene; anti-microbial agents such as triclosan, cephalosporins, aminoglycosides, nitrofurantoin, silver ions, compounds, or salts; bioflim synthesis inhibitors such as non-steroidal anti-inflammatory agents and chelating agents such as ethylenediaminetetraacetic acid, O,O'-bis (2-aminoethyl)ethyleneglycol-N-,N, N',N'-tetra acetic acid and mixtures thereof; antibiotics such as gentamycin, rifampin, monocyclic, and ciprofoixacrin; antibodies including chimeric antibodies and antibody fragments; anesthetic agents such as lidocaine, bupivacaine, and ropivacaine; nitric oxide; nitric oxide (NO) donors such as linsidomine, molsidomine, L-arginine, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warfarin sodium, Dicumarol, aspirin, prostaglandin inhibitors, platelet inhibitors and tick antiplatelet factors; vascular cell growth promoters such as growth factors, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vasoactive mechanisms; and any combinations and prodrugs of the above.

Exemplary biomolecules include peptides, polypeptides and proteins; oligonucleotides; nucleic acids such as double or single stranded DNA (including naked and cDNA), RNA, antisense nucleic acids such as antisense DNA and RNA, small interfering RNA (siRNA), and ribozymes; genes; carbohydrates; angiogenic factors including growth factors; cell cycle inhibitors; and anti-restenosis agents. Nucleic acids may be incorporated into delivery systems such as, for example, vectors (including viral vectors), plasmids or liposomes.

Non-limiting examples of proteins include monocyte chemoattractant proteins ("MCP-1) and bone morphogenic proteins ("BMP's"), such as, for example, BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15. Preferred BMPS are any of BMP-2, BMP-3, BMP-4, BMP-5, BMP-6, and BMP-7. These BMPs can be provided as homodimers, heterodimers, or combinations thereof; alone or together with other molecules. Alternatively, or in addition, molecules capable of inducing an upstream or downstream effect of a BMIP can be provided. Such molecules include any of the "hedgehog" proteins, or the DNA's encoding them. Non-limiting examples of genes include survival genes that protect against cell death, such as anti-apoptotic Bcl-2 family factors and Akt kinase and combinations thereof. Non-limiting examples of angiogenic factors include acidic and basic fibroblast growth factors, vascular endothelial growth factor, epidermal growth factor, transforming growth factor .alpha. and .beta., platelet-derived endothelial growth factor, platelet-derived growth factor, tumor necrosis factor .alpha., hepatocyte growth factor, and insulin like growth factor. A non-limiting example of a cell cycle inhibitor is a cathepsin D (CD) inhibitor. Non-limiting examples of anti-restenosis agents include p15, p16, p18, p19, p21, p27, p53, Rb, nFkB and E2F decoys, thymidine kinase ("TK") and combinations thereof and other agents useful for interfering with cell proliferation.

Exemplary small molecules include hormones, nucleotides, amino acids, sugars, and lipids and compounds have a molecular weight of less than 100 kD.

Exemplary cells include stem cells, progenitor cells, endothelial cells, adult cardiomyocytes, and smooth muscle cells. Cells can be of human origin (autologous or allogenic) or from an animal source (xenogenic), or genetically engineered.

Any of the therapeutic agents may be combined to the extent such combination is biologically compatible.

Any of the above mentioned therapeutic agents may be incorporated into a polymeric coating on the medical device or applied onto a polymeric coating on a medical device. With respect to the type of polymers that may be used in the coating according to the present invention, such polymers may be biodegradable or non-biodegradable. Non-limiting examples of suitable non-biodegradable polymers include polyvinylpyrrolidone including cross-linked polyvinylpyrrolidone; polyvinyl alcohols, copolymers of vinyl monomers such as EVA; polyvinyl ethers; polyvinyl aromatics; polyethylene oxides; polyesters including polyethylene terephthalate; polyamides; polyacrylamides; polyethers including polyether sulfone; polyalkylenes including polypropylene, polyethylene and high molecular weight polyethylene; polyurethanes; polycarbonates, silicones; siloxane polymers; polymer dispersions such as polyurethane dispersions (BAYHDROL®); squalene emulsions; and mixtures and copolymers of any of the foregoing.

Non-limiting examples of suitable biodegradable polymers include polycarboxylic acid, polyanhydrides including maleic anhydride polymers; polyorthoesters; poly-amino acids; polyethylene oxide; polyphosphazenes; polylactic acid, polyglycolic acid and copolymers and mixtures thereof such as poly(L-lactic acid) (PLLA), poly(D,L,-lactide), poly (lactic acid-co-glycolic acid), 50/50 (DL-lactide-co-glycolide); polydioxanone; polypropylene fumarate; polydepsipeptides; polycaprolactone and co-polymers and mixtures thereof such as poly(D,L-lactide-co-caprolactone) and polycaprolactone co-butylacrylate; polyhydroxybutyrate valerate and blends; polycarbonates such as tyrosine-derived polycarbonates and arylates, polyiminocarbonates, and polydimethyltrimethylcarbonates; cyanoacrylate; calcium phosphates; polyglycosaminoglycans; macromolecules such as polysaccharides (including hyaluronic acid; cellulosic polymers such as cellulose, cellulose acetate, and hydroxypropylmethyl cellulose; gelatin; starches; dextrans; alginates and derivatives thereof), proteins and polypeptides; and mixtures and copolymers of any of the foregoing. The biodegradable polymer may also be a surface erodable polymer such as polyhydroxybutyrate and its copolymers, polycaprolactone, polyanhydrides (both crystalline and amorphous), polyorthoesters, maleic anhydride copolymers, and zinc-calcium phosphate.

In a preferred embodiment, the polymer is polyacrylic acid available as HYDROPLUS® (Boston Scientific Corporation, Natick, Mass.), and described in U.S. Pat. No. 5,091,205, the disclosure of which is incorporated by reference herein. In a more preferred embodiment, the polymer is a co-polymer of polylactic acid and polycaprolactone.

Such coatings used with the present invention may be formed by any method known to one in the art. For example, an initial polymer/solvent mixture can be formed and then the therapeutic agent added to the polymer/solvent mixture. Alternatively, the polymer, solvent, and therapeutic agent can be added simultaneously to form the mixture. The polymer/solvent mixture may be a dispersion, suspension or a solution. The therapeutic agent may also be mixed with the polymer in the absence of a solvent. The therapeutic agent may be dissolved in the polymer/solvent mixture or in the polymer to be in a true solution with the mixture or polymer, dispersed into fine or micronized particles in the mixture or polymer, suspended in the mixture or polymer based on its solubility profile, or combined with micelle-forming compounds such as surfactants or adsorbed onto small carrier particles to create a suspension in the mixture or polymer. The coating may comprise multiple polymers and/or multiple therapeutic agents.

The coating can be applied to the medical device by any known method in the art including dipping, spraying, rolling, brushing, electrostatic plating or spinning, vapor deposition, air spraying including atomized spray coating, and spray coating using an ultrasonic nozzle.

The coating is typically from about 1 to about 50 microns thick. In the case of balloon catheters, the thickness is preferably from about 1 to about 10 microns, and more preferably from about 2 to about 5 microns. Very thin polymer coatings, such as about 0.2-0.3 microns and much thicker coatings, such as more than 10 microns, are also possible. It is also within the scope of the present invention to apply multiple layers of polymer coatings onto the medical device. Such multiple layers may contain the same or different therapeutic agents and/or the same or different polymers. Methods of choosing the type, thickness and other properties of the polymer and/or therapeutic agent to create different release kinetics are well known to one in the art.

The medical device may also contain a radio-opacifying agent within its structure to facilitate viewing the medical device during insertion and at any point while the device is implanted. Non-limiting examples of radio-opacifying agents are bismuth subcarbonate, bismuth oxychloride, bismuth trioxide, barium sulfate, tungsten, and mixtures thereof.

Non-limiting examples of medical devices according to the present invention include catheters, guide wires, balloons, filters (e.g., vena cava filters), stents, stent grafts, vascular grafts, intraluminal paving systems, implants and other devices used in connection with drug-loaded polymer coatings. Such medical devices may be implanted or otherwise utilized in body lumina and organs such as the coronary vasculature, esophagus, trachea, colon, biliary tract, urinary tract, prostate, brain, and the like.

While the present invention has been described in connection with the foregoing representative embodiment, it should be readily apparent to those of ordinary skill in the art that the representative embodiment is exemplary in nature and is not to be construed as limiting the scope of protection for the invention as set forth in the appended claims.

What is claimed is:

1. A system for coating an implantable stent having an interior comprising:
    (a) a holding apparatus sized to fit within an implantable stent, wherein the holding apparatus comprises:
        (i) a center support shaft sized to fit within an interior of an implantable medical device;
        (ii) two arbors arranged on the center support shaft in a spaced apart position;
        (iii) a plurality of springs coupled to the two arbors, a first end of at least two of the springs coupled to a first arbor, a second end of at least two of the springs coupled to a second arbor; and
        (iv) an actuator coupled to the center support shaft and adapted to decrease the distance between the two arbors, the decrease of the distance causing a portion of each of the plurality of springs to buckle between the arbors, the buckling of each spring increasing at least one cross-sectional area defined by the holding apparatus, the at least one cross-sectional area being perpendicular to the center support shaft;
    (b) an implantable stent held from the interior by the holding apparatus; and
    (c) a coating apparatus for coating the stent while it is being held from the interior by the holding apparatus.

2. The system according to claim 1, wherein the plurality of springs includes three springs.

3. The system according to claim 1, wherein each spring includes a wire section profile that is one of round, flat, and triangular.

4. The system according to claim 1, wherein the actuator is one of manually actuated, electrically actuated, and pneumatically actuated.

5. The system according to claim 1, wherein actuating the actuator causes at least one of the first and the second arbor to move with respect to the other of the first and the second arbor.

6. The system according to claim 1, wherein actuating the actuator causes the center support shaft to move with respect to at least one of the first and the second arbor.

7. The system according to claim 1, wherein actuating the actuator causes the plurality of springs to expand and to clamp the stent.

8. The system according to claim 1, wherein deactuating the actuator causes the plurality of springs to retract and to release the stent.

9. The system according to claim 1, further comprising a drying rack sized to support the stent after the coating operation and adapted to promote a drying of a coating applied to the stent.

10. The system according to claim 9, further comprising an arrangement for blowing one of air and another gas at the stent to dry the coating.

11. The system according to claim 1, further comprising a lock adapted to secure the actuator in one of an actuated and an unactuated position.

12. The system according to claim 1, further comprising an arrangement for cleaning at least one of the actuator, the center support shaft, the arbors, and the springs, the arrangement for cleaning including at least one of a chemical bath, a chemical spray, and an ultrasonic cleaner.

13. The system according to claim 1, wherein the coating apparatus for coating the stent comprises a spraying arrangement adapted to spray a coating on the stent.

14. The system according to claim 1, wherein the coating apparatus is in fluid communication with a coating source which contains a therapeutic agent.

15. The system according to claim 1, wherein the plurality of springs include leaf springs having a thickness of about 0.0008 inches.

16. The system according to claim 1, further comprising a clasp surrounding a center portion of a spring, the clasp preventing movement of the spring away from the center support.

17. The system according to claim 1, wherein the springs contain barbs positioned to retain the stent on the spring.

18. The system according to claim 1, wherein the stent is coated with a therapeutic agent which includes an antithrombogenic agent.

19. The system according to claim 1, wherein the stent is coated with a therapeutic agent which includes an anti-inflammatory agent.

20. The system according to claim 1, wherein the stent is coated with a therapeutic agent which includes a biomolecule.

21. The system according to claim 1, wherein the stent is less than about 120 mm in length.

22. A system for coating an implantable stent comprising:
(a) a holding apparatus sized to hold an implantable stent from an interior, wherein the holding apparatus comprises at least one elongated support element, the elongated support element having a first end fixed to an arbor and a second end positioned proximate to an anchor point;
(b) an implantable stent held from the interior by the holding apparatus; and
(c) a coating apparatus for coating the stent while it is being held from the interior by the holding apparatus;
wherein the elongated support element is adapted such that causing the first end and the second end of the elongated support element to become closer relative to each other causes a portion of the elongated support element to buckle between the arbor and the anchor point to hold the stent from the interior and to increase at least one cross-sectional area defined by the holding apparatus,
wherein the elongated support element is adapted such that causing the first end and the second end of the elongated support element to become farther apart causes the elongated support element to straighten to release the stent and wherein the support element is sized to fit within an interior surface of the stent;

23. The system according to claim 22, wherein the stent is less than about 120 mm in length.

24. A system for coating a medical device comprising:
a holding apparatus for holding the medical device from an interior, wherein the holding apparatus comprises:
(i) a center support shaft;
(ii) two arbors arranged on the center support shaft in a spaced apart position;
(iii) a plurality of springs coupled to the two arbors, a first end of each of the springs coupled to a first arbor, a second end of each of the springs coupled to a second arbor; and
(iv) an actuator wire coupled to the center support shaft and adapted to decrease the distance between the two arbors, the decrease of the distance causing a portion of each of the plurality of springs to buckle between the arbors, the buckling of each spring increasing at least one cross-sectional area defined by the device, the at least one cross-sectional area being perpendicular to the center support shaft; and
a coating apparatus for coating the medical device while it is being held from the interior by the holding apparatus.

25. A system for coating a medical device comprising:
a holding apparatus for holding the medical device from an interior, wherein the holding apparatus comprises:
(i) a center support shaft;
(ii) two arbors arranged on the center support shaft in a spaced apart position;
(iii) a plurality of springs coupled to the two arbors, a first end of each of the springs coupled to a first arbor, a second end of each of the springs coupled to a second arbor; and
(iv) an actuator coupled to the center support shaft and adapted to decrease the distance between the two arbors, the decrease of the distance causing a portion of each of the plurality of springs to buckle in at least one buckle region between the arbors, the buckling of each spring increasing at least one cross-sectional area defined by the device, the at least one cross-sectional area being perpendicular to the center support shaft; and
a coating apparatus for coating the medical device while it is being held from the interior by the holding apparatus,
wherein the holding apparatus further comprises a center actuating wire situated inside the center support shaft and coupled to the actuator and the two arbors and adapted to decrease the distance between the two arbors, wherein, when the actuator is actuated, the plurality of springs are compressed and each spring buckles in the at least one buckle region.

26. The system according to claim 25, wherein one of the first and the second arbor is adapted to be controlled by the center actuating wire to cause the distance between the first and the second arbor to one of decrease and increase.

27. A system for coating a medical device comprising:
a holding apparatus for holding the medical device from an interior, wherein the holding apparatus comprises:
(i) a center support shaft;
(ii) two arbors arranged on the center support shaft in a spaced apart position;
(iii) a plurality of springs coupled to the two arbors, a first end of each of the springs coupled to a first arbor, a second end of each of the springs coupled to a second arbor; and
(iv) an actuator coupled to the center support shaft and adapted to decrease the distance between the two arbors, the decrease of the distance causing a portion of each of the plurality of springs to buckle in at least one buckle region between the arbors, the buckling of each spring increasing at least one cross-sectional area defined by the device, the at least one cross-sectional area being perpendicular to the center support shaft; and
a coating apparatus for coating the medical device while it is being held from the interior by the holding apparatus,
wherein the holding apparatus further comprises at least one clasp assigned to at least one spring and arranged between the first and the second arbors, the at least one clasp coupling the at least one spring to the center support shaft, wherein the at least one clasp defines a plurality of buckle regions for the at least one spring, the number of buckle regions equal to the number of clasps plus one.

28. The system according to claim 27, wherein one clasp is assigned to all springs and is arranged centrally between the first and the second arbors.

29. The system according to claim 27, wherein the at least one clasp includes at least two clasps arranged at different positions on the central support shaft, a first plurality of buckle regions defined by a first clasp being out of phase with a second plurality of buckle regions defined by a second clasp.

30. A system for coating a medical device comprising:
a holding apparatus for holding the medical device from an interior, wherein the holding apparatus comprises:
(i) a center support shaft;
(ii) two arbors arranged on the center support shaft in a spaced apart position;
(iii) a plurality of springs coupled to the two arbors, a first end of each of the springs coupled to a first arbor, a second end of each of the springs coupled to a second arbor; and
(iv) an actuator coupled to the center support shaft and adapted to decrease the distance between the two arbors, the decrease of the distance causing a portion of each of the plurality of springs to buckle between the arbors, the buckling of each spring increasing at least one cross-sectional area defined by the device, the at least one cross-sectional area being perpendicular to the center support shaft; and
a coating apparatus for coating the medical device while it is being held from the interior by the holding apparatus,
wherein the holding apparatus further comprises a collect coupled to the center support shaft and wherein an end effector of a robot is coupled to the collect.

31. A system for coating an implantable stent having an interior comprising:
(a) a holding apparatus sized to fit within an implantable stent, wherein the holding apparatus comprises:
(i) a center support shaft sized to fit within an interior of an implantable medical device;
(ii) two arbors arranged on the center support shaft in a spaced apart position;
(iii) a plurality of springs coupled to the two arbors, a first end of at least two of the springs coupled to a first arbor, a second end of at least two of the springs coupled to a second arbor; and
(iv) an actuator coupled to the center support shaft and adapted to decrease the distance between the two arbors, the decrease of the distance causing a portion of each of the plurality of springs to buckle between the arbors, the buckling of each spring increasing at least one cross-sectional area defined by the holding apparatus, the at least one cross-sectional area being perpendicular to the center support shaft;
(b) an implantable stent having an interior surface and an exterior surface, the implantable stent held from the interior by the holding apparatus; and
(c) means for coating the exterior surface and the interior surface of the stent while it is being held from the interior of the holding apparatus.

* * * * *

UNITED STATES PATENT AND TRADEMARK OFFICE
CERTIFICATE OF CORRECTION

PATENT NO. : 7,306,677 B2  Page 1 of 1
APPLICATION NO. : 10/769397
DATED : December 11, 2007
INVENTOR(S) : Robida

It is certified that error appears in the above-identified patent and that said Letters Patent is hereby corrected as shown below:

Title Page item 73

Assignee should be changed from "Boston Scientific Corporation" to --Boston Scientific Scimed, Inc.--.

Signed and Sealed this

Fourteenth Day of July, 2009

JOHN DOLL
*Acting Director of the United States Patent and Trademark Office*